United States Patent [19]
Yamamoto et al.

[11] Patent Number: 5,260,468
[45] Date of Patent: Nov. 9, 1993

[54] PREPARATION OF HYDROGENSILOXANES

[75] Inventors: Yasushi Yamamoto, Takasaki; Hideki Fujii, Annaka, both of Japan

[73] Assignee: Shin-Etsu Chemical Co., Ltd., Tokyo, Japan

[21] Appl. No.: 823,766

[22] Filed: Jan. 22, 1992

[30] Foreign Application Priority Data

Jan. 24, 1991 [JP] Japan .................................. 3-024199

[51] Int. Cl.$^5$ ................................................ C07F 7/08
[52] U.S. Cl. ....................... 556/431; 556/435; 556/444
[58] Field of Search ................ 556/444, 435, 431

[56] References Cited

U.S. PATENT DOCUMENTS

| | | | |
|---|---|---|---|
| 3,218,344 | 11/1965 | Bailey et al. | 556/444 |
| 3,542,830 | 11/1970 | Kim et al. | 556/444 X |
| 3,576,023 | 4/1971 | Curry | 260/448.2 |
| 3,647,740 | 3/1972 | Loree et al. | 556/435 X |
| 4,057,566 | 11/1977 | Carter et al. | 260/448.2 |

FOREIGN PATENT DOCUMENTS

| | | |
|---|---|---|
| 208239 | 1/1987 | European Pat. Off. |
| 435654 | 7/1991 | European Pat. Off. |
| 1936069 | 2/1970 | Fed. Rep. of Germany |
| 2337731 | 1/1977 | France |

OTHER PUBLICATIONS

Zhurnal Obshchei Khimii: vol. 47, No. 1, 1977, pp. 117–121.

Nikolaev, G. A. et al.: "Heterofunctional-Condensation Reactions Between Chloro- and Alkoxy-Silanes". Chemical Abstracts, vol. 113; 1990; Abstract No. 152748Q; Shin-Etsu Chemical Industry Co., Ltd; Fluoroalkyl-Containing Organic Silicon Compounds.

*Primary Examiner*—Paul F. Shaver
*Attorney, Agent, or Firm*—Birch, Stewart, Kolasch & Birch

[57] ABSTRACT

There is provided a process for preparing a hydrogensiloxane of the following general formula (2):

$$(HSiO)_n \underset{CH_3}{\underset{|}{\overset{CH_3(CH_3)_{3-n}}{\overset{|}{Si}}}} CH_2CH_2(CH_2OCH_2)_p R_f (CH_2OCH_2)_p CH_2CH_2 \underset{CH_3}{\underset{|}{\overset{(CH_3)_{3-n}}{\overset{|}{\underset{CH_3}{Si}}}}} (OSiH)_n \quad (2)$$

wherein Rf is a perfluoropolyether or perfluoroalkylene group, n is equal to 1, 2 or 3, and p is equal to 0 or 1, said process comprising the step of hydrolyzing a chlorosilane of the following general formula (1):

$$Cl_n \overset{(CH_3)_{3-n}}{\underset{|}{Si}} CH_2CH_2(CH_2OCH_2)_p R_f (CH_2OCH_2)_p CH_2CH_2 \overset{(CH_3)_{3-n}}{\underset{|}{Si}} Cl_n \quad (1)$$

wherein Rf, n and p are as defined above, along with 1,1,3,3-tetramethyldisiloxane.

16 Claims, 2 Drawing Sheets

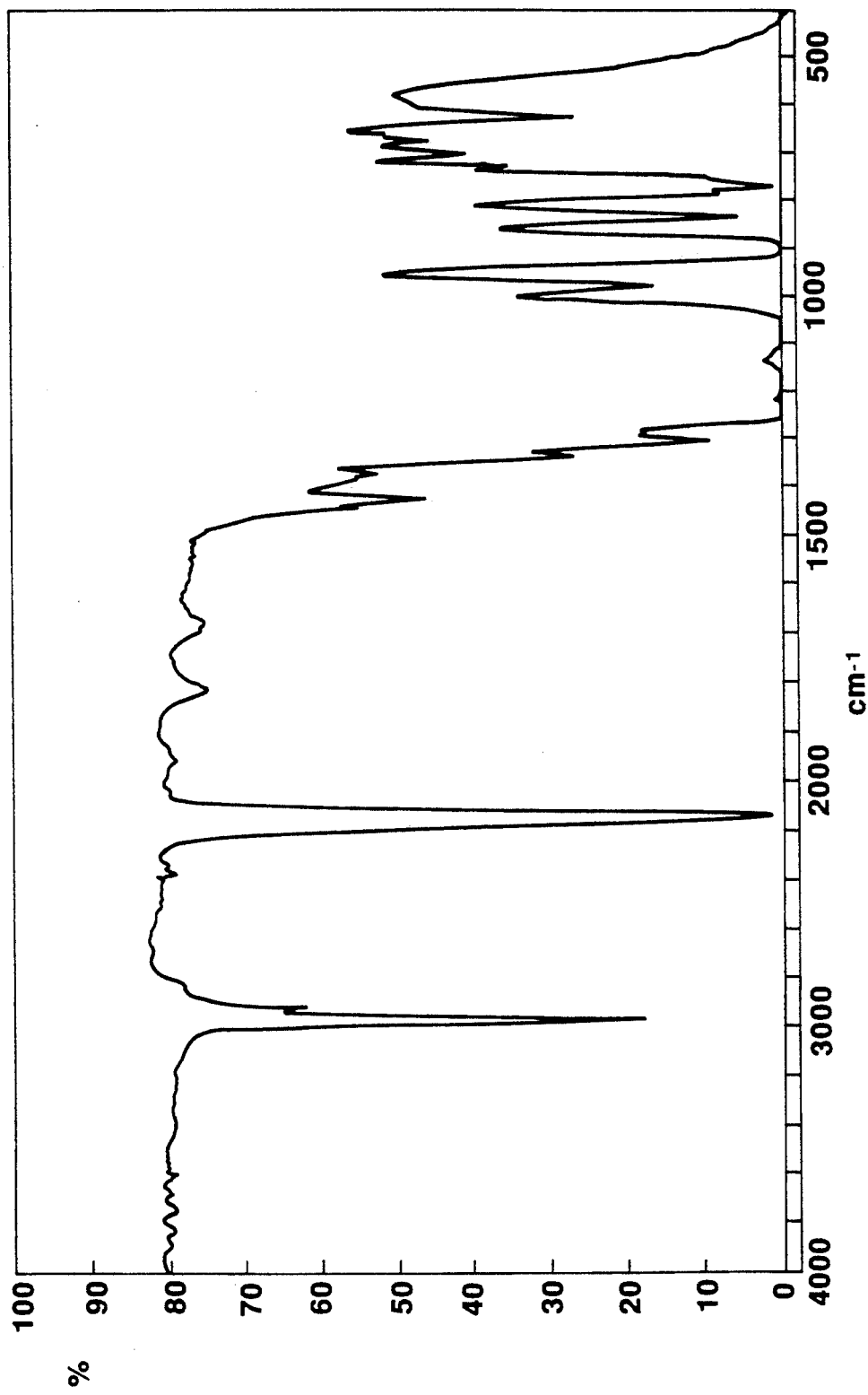

PREPARATION OF HYDROGENSILOXANES

This invention relates to a process for preparing hydrogensiloxanes suitable for use as crosslinking agents.

BACKGROUND OF THE INVENTION

In the prior art, a variety of hydrogensiloxanes were proposed as well as their preparation processes. Japanese Patent Application Kokai Nos. 47605/1987,

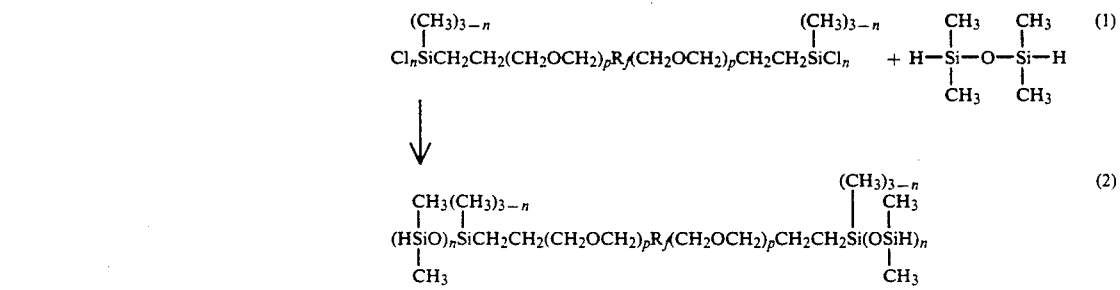

47608/1987 and 49305/1987 disclose hydrogensiloxanes of formula (3), which are synthesized by hydrolyzing a solution of a chlorosilane of formula (4) and dimethylchlorosilane of formula (5) in trifluorotrichloroethane.

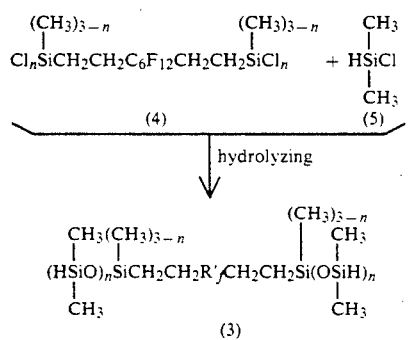

In the formulae, R'f is $C_6F_{12}$ which is a perfluoroalkylene group, and n is equal to 1, 2 or 3.

Dimethylchlorosilane of formula (5) forms in a minor amount during preparation of silicones by the direct process, but is very difficult to separate and isolate from low boiling fractions of hydrocarbon. Another known process for the synthesis of dimethylchlorosilane of formula (5) is by reacting dichlorosilane with 1,1,3,3-tetramethyldisiloxane in the presence of a catalyst. In either case, dimethylchlorosilane is available at an increased cost and less advantageous as a source material. The possibility that the dimethylchlorosilane of formula (5) condense into polysiloxane by-products is also a problem.

The above-referred patent publications disclose specific examples of synthesizing hydrogensiloxanes of formula (3) wherein R'f is a perfluoroalkylene group, but not hydrogensiloxanes wherein R'f is a perfluoropolyether group. In this regard, hydrogensiloxanes of formula (3) wherein R'f is a perfluoropolyether group are not disclosed in a substantial sense.

SUMMARY OF THE INVENTION

Therefore, an object of the present invention is to provide a novel and improved process for preparing hydrogensiloxanes having a fluorinated polyether group as well as a fluorinated alkylene group in a commercially advantageous manner without using dimethylchlorosilane.

The inventors have found that by hydrolyzing a chlorosilane of formula (1) along with 1,1,3,3-tetramethyldisiloxane, preferably in aqueous hydrochloric acid, there is obtained a hydrogensiloxane of formula (2). Therefore, the hydrogensiloxane is obtained in high yields, without using expensive dimethylchlorosilane, while eliminating the formation of polysiloxane by-products through condensation.

In the formulae, Rf is a perfluoropolyether or perfluoroalkylene group, n is equal to 1, 2 or 3, and p is equal to 0 or 1.

Therefore, the present invention provides a process for preparing a hydrogensiloxane of formula (2) by hydrolyzing a chlorosilane of formula (1) along with 1,1,3,3-tetramethyldisiloxane.

DETAILED DESCRIPTION OF THE INVENTION

Figure 1:
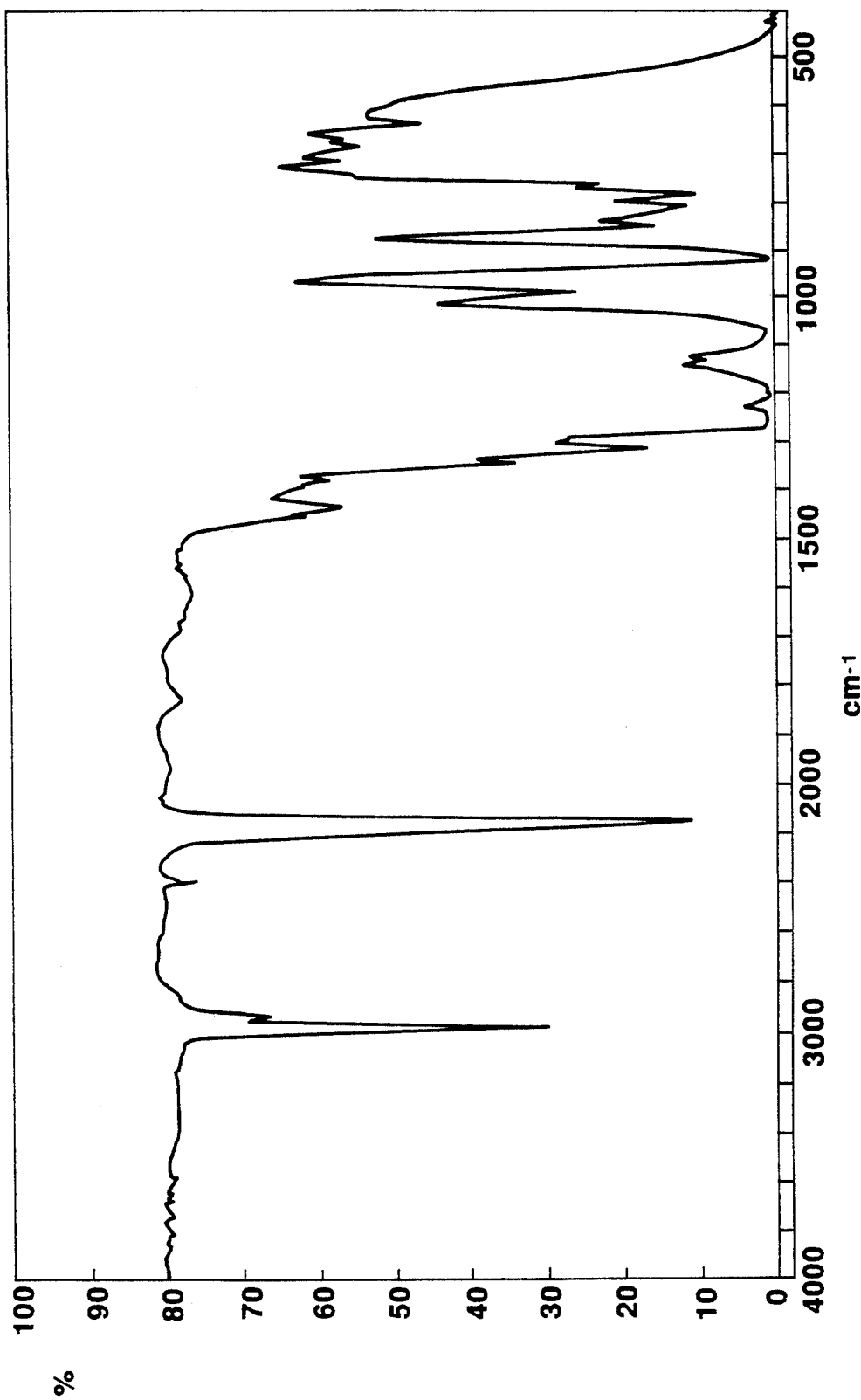
FIGS. 1. and 2 are infrared absorption spectra of the hydrogensiloxanes obtained in Examples 1 and 2.

The hydrogensiloxane preparing process according to the present invention starts with a chlorosilane of formula (1).

$$\underset{|}{\text{Cl}_n\text{SiCH}_2\text{CH}_2(\text{CH}_2\text{OCH}_2)_p\text{R}_f(\text{CH}_2\text{OCH}_2)_p\text{CH}_2\text{CH}_2\text{SiCl}_n} \quad (1)$$
$$(\text{CH}_3)_{3-n} \qquad\qquad\qquad (\text{CH}_3)_{3-n}$$

In the formula, Rf is a perfluoropolyether or perfluoroalkylene group, n is equal to 1, 2 or 3, and p is equal to 0 or 1.

Often, the perfluoropolyether group represented by Rf has 4 to 15 carbon atoms. Preferred perfluoropolyether groups are of formula (6).

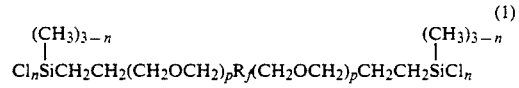

In the formula, x and y each are equal to o, 1 or 2, the sum of x and y ranges from 0 to 3, and X is F or $CF_3$. Several illustrative examples of the perfluoropolyether group represented by Rf are given below.

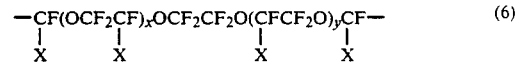

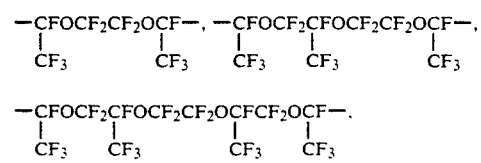

-continued

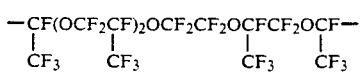

Preferred perfluoroalkylene groups represented by Rf are those having 2 to 10 carbon atoms as represented by —$C_zF_{2z}$— wherein z is an integer of from 2 to 10, for example, —$C_2F_4$—, —$C_4F_8$—, —$C_6F_{12}$—, —$C_8F_{16}$—, etc.

According to the present invention, a hydrogensiloxane of formula (2) is produced by hydrolyzing a chlorosilane of formula (1) along with 1,1,3,3-tetramethyldisiloxane, preferably in aqueous hydrochloric acid.

The amount of 1,1,3,3-tetramethyldisiloxane used in the process is generally such that there is available from about 1 to 5 mol, preferably from about 1.1 to 1.5 mol of $HSi(CH_3)_2O_\frac{1}{2}$ unit per mol of SiCl in the chlorosilane of formula (1). The amounts of water and hydrochloric acid used are not particularly limited insofar as they are sufficient to hydrolyze the chlorosilane of formula (1) and to catalyze reaction of the resulting silanol with 1,1,3,3-tetramethyldisiloxane. Preferably, water is used in an amount of about 1 to 3 mol per mol of SiCl in the chlorosilane of formula (1), and the amount of conc. hydrochloric acid used is about 1 to 3 times the weight of water.

The reaction temperature may vary insofar as the acid-assisted equilibration and Si—H decomposition can be restrained. Often, the temperature is below room temperature, preferably from about 0° C. to about 15° C. The reaction time generally ranges from about 2 to about 5 hours.

In the practice of the invention, a water-insoluble organic solvent may be used which is not reactive with hydrogen chloride and hydrogensiloxane. For example, when a starting chlorosilane such as $Cl_3SiCH_2CH_2C_6F_{12}CH_2CH_2SiCl_3$ is crystalline and difficult to add dropwise, it is convenient to dissolve the chlorosilane in α,α,α,α',α',α'-hexafluoro-m-xylene. The use of organic solvent is also effective where separation from water is difficult during post treatment. In most cases, however, 1,1,3,,3-tetramethyldisiloxane and the product play the role of solvent. Therefore, it is not recommended to use a solvent in the present reaction system because the used solvent adds to the disposal load. Also, although it is a common practice to accelerate hydrolysis by adding a water-miscible organic solvent such as methanol and ethanol as often employed in general hydrolysis processes, it is not necessary to add alcohol to the present reaction system partly because the hydrolysis reaction is fast enough and partly because the disposal of used water should be simple.

EXAMPLE

Examples of the present invention are given below by way of illustration and not by way of limitation.

EXAMPLE 1

A four-necked flask was charged with 42 grams (0.31 mol) of 1,1,3,3-tetramethyldisiloxane, 9 grams of water, and 25 grams of conc. hydrochloric acid, and cooled at 5° to 10° C. with an ice water bath. With thorough stirring, 100 grams (0.128 mol) of a silane of formula (7) was added dropwise to the flask over 3 hours. At the end of addition, the reaction mixture was continuously stirred for a further one hour. Then 200 ml of water was carefully added to the reaction mixture such that the mixture might not exceed a temperature of 20° C.

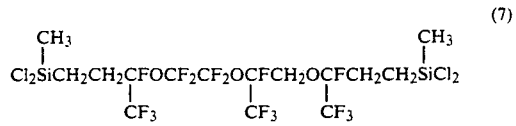
(7)

The organic layer was washed twice with water, twice with 5% sodium bicarbonate aqueous solution, and finally 5 times with water, dried over $Na_2SO_4$, and distilled in vacuum. A fraction at 150°–153° C./$1.0 \times 10^{-5}$ mmHg provided 108 grams (yield 90%) of a hydrogensiloxane of formula (8). It was identified by a series of analysis results to have the following structure.

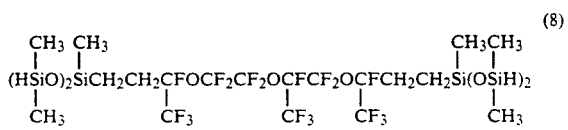
(8)

Elemental Analysis

|  | C | H | Si |
| --- | --- | --- | --- |
| Calcd.*, % | 29.4 | 4.5 | 17.9 |
| Found. % | 29.3 | 4.3 | 18.0 |

*based on $C_{23}H_{42}F_{18}O_7Si_6$

GCMS: 940
IR spectrum: FIG. 1
A characteristic absorption peak attributable to SiH appeared at a wave-number of 2140 cm$^{-1}$.
NMR spectrum:
internal standard: chloroform

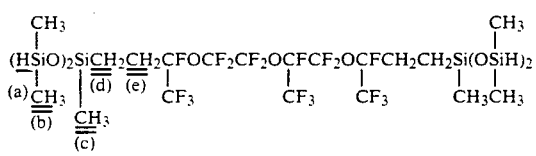

a: δ=4.50–4.90 ppm (—SiH, m, 4H)
b: δ=0.19–0.23 ppm (—SiCH$_3$, d, 24H)
c: δ=0.12 ppm (—SiCH$_3$, s, 6H)
d: δ=0.50–0.97 ppm (SiCH$_2$, m, 4H)
e: δ=1.83–2.57 ppm (CH$_2$CF, m, 4H)

EXAMPLE 2

As in Example 1, 165 grams (0.2 mol) of a silane of formula (9) was hydrolyzed in a mixture of 134 grams (1.0 mol) of 1,1,3,3-tetramethyldisiloxane, 20 grams of water, and 50 grams of conc. hydrochloric acid.

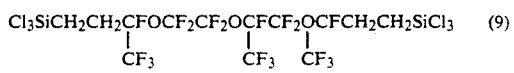
(9)

Vacuum distillation provided 182 grams (yield 86%) of a hydrogensiloxane of formula (10) as a fraction at 160°–162° C./$1.0 \times 10^{-5}$ mmHg. It was identified by a series of analysis results to have the following structure.

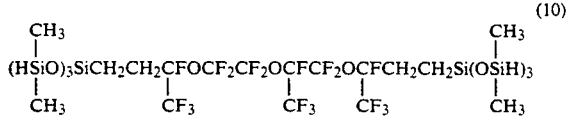

(10)

Elemental Analysis

|  | C | H | Si |
|---|---|---|---|
| Calcd.*, % | 28.5 | 4.0 | 21.3 |
| Found, % | 28.7 | 4.1 | 21.1 |

*based on $C_{25}H_{50}F_{18}O_9Si_8$

GCMS: 1060
IR spectrum: FIG. 2
A characteristic absorption peak attributable to SiH appeared at a wave-number of 2140 cm$^{-1}$.
NMR spectrum:
internal standard: chloroform

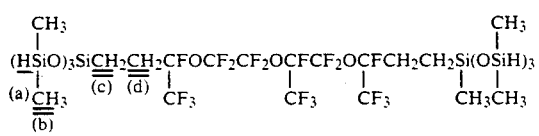

a: δ=4.63–4.98 ppm (—SiH, m, 6H)
b: δ=0.26–0.31 ppm (—SiCH$_3$, d, 36H)
c: δ=0.53–1.03 ppm (SiCH$_2$, m, 4H)
d: δ=1.90–2.57 ppm (CH$_2$CF, m, 4 H)

EXAMPLE 3

As in Example 1, 198 grams (0.2 mol) of a silane of formula (11) was hydrolyzed in a mixture of 134 grams (1.0 mol) of 1,1,3,3-tetramethyldisilazane, 20 grams of water, and 50 grams of conc. hydrochloric acid.

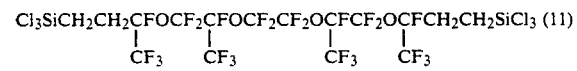

There was obtained 216 grams (yield 88%) of a hydrogensiloxane of formula (12). It was purified by preparative liquid chromatography and identified by a series of analysis results to have the following structure.

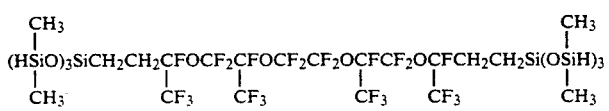

Elemental Analysis

|  | C | H | Si |
|---|---|---|---|
| Calcd.*, % | 27.4 | 4.1 | 18.3 |
| Found, % | 27.2 | 4.2 | 18.4 |

*based on $C_{28}H_{50}F_{24}O_{10}Si_8$

GCMS: 1226
IR spectrum:
A characteristic absorption peak attributable to SiH appeared at a wave-number of 2140 cm$^{-1}$.
NMR spectrum:
internal standard: chloroform

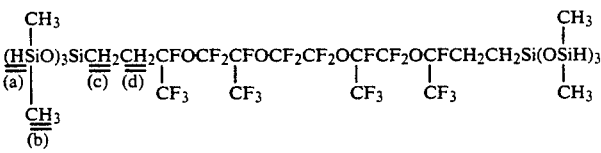

a: δ=4.64–5.00 ppm (SiH, m, 6H)
b: δ=0.25–0.31 ppm (—CH$_3$, d, 36H)
c: δ=0.51–1.02 ppm (CH$_2$, m, 4H)
d: δ=1.92–2.60 ppm (CH$_2$, m, 4H)

As in Example 1, 250 grams (0.4 mol) of a silane of formula (13) in 200 ml of α,α,α,α',α',α'-hexafluoro-m-xylene was added dropwise to a mixture of 268 grams (2.0 mol) of 1,1,3,3-tetramethyldisiloxane, 40 grams of water, and 100 grams of conc. hydrochloric acid for hydrolysis.

Vacuum distillation provided 316 grams (yield 92%) of a hydrogensiloxane of formula (14) as a fraction at 147°–150° C./1.2×10$^{-5}$ mmHg. It was identified to have the following structure by a comparison with a standard sample.

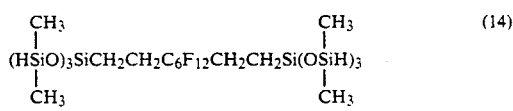

There has been described a commercially advantageous process for preparing hydrogensiloxanes without using dimethylchlorosilane which is expensive and would form by-products during reaction. The thus obtained hydrogensiloxanes are versatile crosslinking agents which are effective not only for addition type fluorosilicones, but also for general silicones and even resins other than silicones.

Although some preferred embodiments have been described, many modifications and variations may be made thereto in the light of the above teachings. It is therefore to be understood that within the scope of the appended claims, the invention may be practiced otherwise than as specifically described.

We claim:
1. A process for preparing a hydrogen-siloxane of the following general formula (2):

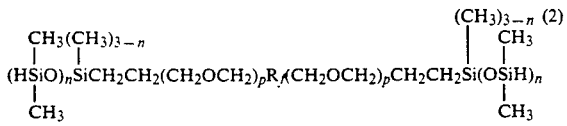

wherein Rf is a perfluoropolyether or perfluoroalkylene group, n is equal to 1, 2 or 3, and p is equal to 0 or 1, said process comprising the step of hydrolyzing a chlorosilane of the following general formula (1):

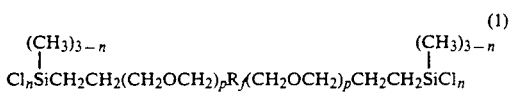

wherein Rf, n and p are as defined above, along with 1,1,3,3-tetramethyldisiloxane, wherein the hydrolysis is carried out in aqueous hydrochloric acid.

2. The process of claim 1, wherein Rf is a perfluoropolyether group having 4 to 15 carbon atoms.

3. The process of claim 1 wherein Rf is a perfluoroalkylene group having 2 to 10 carbon atoms.

4. The process of claim 1, wherein Rf is a perfluoropolyether group of formula (6)

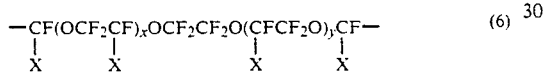

wherein x and y each are equal to 0, 1 or 2; the sum of x and y ranges from 0 to 3; and X is F or $CF_3$.

5. The process of claim 1, wherein Rf is a perfluoropolyether group selected from the group consisting of

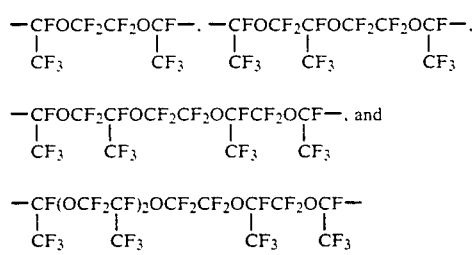

6. The process of claim 1, wherein Rf is a perfluoroalkylene group represented by $-C_zF_{2z}-$, wherein z is an integer of from 2 to 10.

7. The process of claim 1, wherein Rf is a perfluoroalkylene group selected from the group consisting of $-C_2F_4-$, $-C_4F_8-$, $-C_6F_{12}-$, and $-C_8F_{16}-$.

8. The process of claim 1, wherein 1,1,3,3-tetramethyldisiloxane is present in an amount of from 1 to 5 mol of $HSi(CH_3)_2O_{\frac{1}{2}}$ unit per mol of SiCl in the chlorosilane of formula (1).

9. The process of claim 1, wherein 1,1,3,3-tetramethyldisiloxane is present in an amount of from 1.1 to 1.5 mol of $HSi(CH_3)_2O_{\frac{1}{2}}$ unit per mol of SiCl in the chlorosilane of formula (1).

10. The process of claim 1, wherein water is present in an amount of from 1 to 3 mol per mol of SiCl in the chlorosilane of formula (1) and wherein the hydrochloric acid in its concentrated form is present in an amount of about 1 to 3 times the weight of water.

11. The process of claim 1, wherein the hydrolysis is conducted at a reaction temperature of from 0° C. to 15° C.

12. The process of claim 1, wherein the hydrolysis is conducted during a reaction time of from 2 to about 5 hours.

13. A process for preparing a hydrogen-siloxane of the following general formula (2):

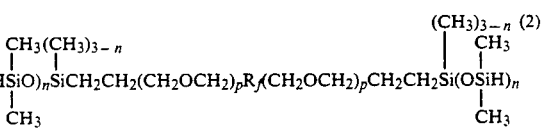

wherein Rf is a perfluoropolyether or perfluoroalkylene group, n is equal to 1, 2 or 3, and p is equal to 0 or 1, said process comprising the step of hydrolyzing a chlorosilane of the following general formula (1):

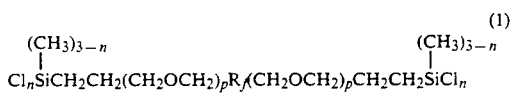

wherein Rf, n and p are as defined above, along with 1,1,3,3-tetramethyldisiloxane, wherein the hydrolysis is carried out in aqueous hydrochloric acid, wherein 1,1,3,3-tetramethyldisiloxane is present in an amount of from 1 to 5 mol of $HSi(CH_3)_2O_{\frac{1}{2}}$ unit per mol of SiCl in the chlorosilane of formula (1); wherein water is present in an amount of from 1 to 3 mol per mol of SiCl in the chlorosilane of formula (1); wherein the hydrochloric acid in its concentrated form is present in an amount of about 1 to 3 times the weight of water; and wherein the hydrolysis is conducted at a reaction temperature of from 0° C. to 15° C..

14. The process of claim 13, wherein 1,1,3,3-tetramethyldisiloxane is present in an amount of from 1.1 to 1.5 mol of $HSi(CH_3)_2O_{\frac{1}{2}}$ unit per mol of SiCl in the chlorosilane of formula (1).

15. The process of claim 13, wherein Rf is a perfluoropolyether group of formula (6)

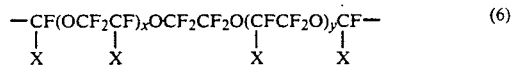

wherein x and y each are equal to 0, 1 or 2; the sum of x and y ranges from 0 to 3; and X is F or $CF_3$.

16. The process of claim 13, wherein Rf is a perfluoroalkylene group represented by $-C_zF_{2z}-$, wherein z is an integer of from 2 to 10.

* * * * *